United States Patent [19]

Weiguny et al.

[11] Patent Number: 5,585,523
[45] Date of Patent: Dec. 17, 1996

[54] PROCESS FOR THE PREPARATION OF ALDEHYDES BY CATALYTIC GAS PHASE HYDROGENATION OF CARBOXYLIC ACID OR THEIR DERIVATIVES WITH THE AID OF A TIN CATALYST

[75] Inventors: Jens Weiguny, Weiterstadt; Holger Borchert, Frankfurt; Thomas Gerdau, Eppstein, all of Germany

[73] Assignee: Hoechst Aktiengesellschaft, Frankfurt, Germany

[21] Appl. No.: 524,345

[22] Filed: Sep. 6, 1995

[30] Foreign Application Priority Data

Sep. 8, 1994 [DE] Germany ................ 44 31 987.8

[51] Int. Cl.$^6$ ...................................... C07C 45/41
[52] U.S. Cl. ................ 568/435; 568/484; 568/420; 568/449
[58] Field of Search ................ 568/485, 426, 568/435, 484, 420, 449

[56] References Cited

U.S. PATENT DOCUMENTS

| | | | |
|---|---|---|---|
| 4,328,373 | 5/1982 | Stiojny | 568/435 |
| 4,521,630 | 6/1985 | Wattimena et al. | 568/484 |
| 4,585,899 | 4/1986 | Gelbein | 568/484 |
| 4,613,700 | 9/1986 | Maki et al. | 568/435 |
| 4,950,799 | 4/1990 | Haigis | 568/484 |
| 5,059,716 | 10/1991 | Joentgen | 568/484 |
| 5,334,769 | 8/1994 | Fehrero et al. | 568/484 |

FOREIGN PATENT DOCUMENTS 617432  11/1926  France ................ 568/485

OTHER PUBLICATIONS

European Search Report No. 95113495.6, Dec. 18, 1995.

*Primary Examiner*—James H. Reamer
*Attorney, Agent, or Firm*—Connolly and Hutz

[57] ABSTRACT

Process for the preparation of aldehydes by catalytic gas phase hydrogenation of carboxylic acid or their derivatives with the aid of a tin catalyst The invention relates to a process for the preparation of aldehydes by catalytic gas phase hydrogenation of carboxylic acids or carboxylic acid derivatives at elevated temperature, which comprises employing at tin catalyst supplied to an oxidic support material.

22 Claims, No Drawings

PROCESS FOR THE PREPARATION OF ALDEHYDES BY CATALYTIC GAS PHASE HYDROGENATION OF CARBOXYLIC ACID OR THEIR DERIVATIVES WITH THE AID OF A TIN CATALYST

The present invention relates to a process for the preparation of aromatic and aliphatic aldehydes by catalytic gas phase hydrogenation of aromatic and aliphatic carboxylic acids or their derivatives with the aid of a tin catalyst.

The preparation of aromatic or aliphatic aldehydes by reduction of the corresponding carboxylic acids with molecular hydrogen over various catalysts is known. The oldest technique goes back to U.S. Pat. No. 3,935,265, in which alkyl esters of aromatic carboxylic acids are reacted with hydrogen over aluminum oxide at 400° to 600° C. to give aromatic aldehydes. For example, benzaldehyde is obtained from methylbenzoate with a selectivity of 37% at a conversion of 39%.

It is furthermore known that zirconium dioxide, by itself or doped with oxides of other metals, such as chromium, manganese, iron, zinc, cobalt, bismuth, lead, rhenium or elements of main group III, such as boron, aluminum, gallium, indium or thallium (EP 150961), or together with oxides or elements of the lanthanide group (U.S. Pat. No. 4,328,373), is capable of hydrogenating carboxylic acids or derivatives thereof to give the corresponding aldehydes. According to U.S. Pat. No. 4,328,373, as well as zirconium oxide, oxides of yttrium, cerium, praseodymium, thorium and uranium on aluminum oxide can be employed. EP 573087 describes a catalyst which comprises the oxides of aluminum, manganese, zinc and copper and is prepared by coprecipitation of the corresponding salts.

The use of tin oxides for the reduction of carboxylic acids with hydrogen to give the corresponding aldehydes is described in U.S. Pat. No. 4,950,799 and in EP 539274. According to U.S. Pat. No. 4,950,799, a $V_2O_5/SnO_2$ mixed oxide catalyst, which can be applied to a support, such as, for example, the oxides of aluminum, titanium, iron, manganese, zirconium, chromium, lead or cobalt, was used for reduction of m-phenoxybenzoic acid. The selectivity, based on the aldehyde, was only 44% at a conversion of 54%. EP 539274 describes the hydrogenation of carboxylic acids using a bimetallic catalyst of the type $Ru-Sn-B/\gamma-Al_2O_3$. Thus, for example, benzoic acid can be converted into benzaldehyde with a selectivity of 76% at a conversion of 76%. In both cases, the yield of aldehyde is in a range which is industrially unacceptable, and furthermore complicated multi-component systems, the preparation of which also requires expensive starting materials in the case of EP 539 274, are employed as the catalyst.

There is thus a need for a process which avoids the disadvantages mentioned, which operates with a readily accessible and inexpensive catalyst system and which produces the aldehydes in a high yield and purity.

This object is achieved by a process for the preparation of aldehydes by catalytic gas phase hydrogenation of carboxylic acids or carboxylic acid derivatives at elevated temperature, which comprises employing a tin catalyst applied to an oxidic support material.

The catalyst system to be employed according to the invention can be prepared by simple processes from readily accessible materials and gives very good space/time yields for the hydrogenation of acids. The use of a complicated multi-component system and the use of expensive starting substances, such as zirconium dioxide and rare earth metals, is avoided.

Suitable oxidic support materials are, for example, aluminum oxide, zirconium oxide, iron oxide, titanium oxide or yttrium oxide, aluminum oxide being particularly advantageous for reasons of cost.

The catalyst system which can be employed according to the invention can be prepared by impregnation or coprecipitation and subsequent drying and calcining. In the first case, a solution of a suitable tin compound is applied to the chosen support, which can be in the form of an oxide or hydroxide, by spraying or by soaking. The tin can be present in the compounds both as Sn(II) and as Sn(IV). Suitable compounds are, for example, tin halides, tin sulphates, tin oxalates, tin carboxylates, tin alkoxides, tin hydroxides and di-tin and organotin compounds. The impregnated supports are then dried at 100° to 150° C., preferably at 130° C. and calcined at 400° to 900° C., preferably at 500° to 700° C. The catalysts thus prepared can be further processed to pellets or extrudates by the customary processes.

In the second case, suitable metal salts of the support materials and suitable tin compounds can be coprecipitated at pH values of 6 to 10. The choice of metal salts depends on the availability of the salts for the corresponding catalyst. For example, the nitrate is preferred in the case of aluminum, while the oxynitrate or oxydichloride is suitable in the case of zirconium. After the precipitation, the hydroxides are filtered off and washed with a suitable solvent. Drying is carried out at 100° to 150° C., preferably at 130° C., if appropriate by applying a vacuum, and calcining is carried out at 400° to 900° C., preferably at 500° to 700° C. A suitable time for the calcining is 2 to 10 hours. The tin catalyst thus prepared is in the form of granules and can be employed directly in the reaction after comminution to the desired particle size.

In many cases, it has proved appropriate to employ the tin in an atomic ratio to the support of 0.001/1 to 0.5/1, preferably 0.005/1 to 0.2/1.

Before the reduction of the carboxylic acids, it is advantageous to preform the catalyst at higher temperatures with a suitable reducing agent. The hydrogenation reaction of the carboxylic acids can be carried out in a continuous or batchwise procedure. It has proved favorable to work at a temperature of 250° to 600° C., in particular 300° to 400° C., under a pressure of 0.1 to 10 bar, in particular under atmospheric pressure. The hydrogenation can be carried out with molecular hydrogenation, which can also be prepared in situ. It is also possible to dilute the hydrogen with an inert gas, such as nitrogen or argon. The carboxylic component can be fed to an evaporator as a solid, as a melt or as a solution in a suitable solvent, such as benzene, toluene, xylene or cyclohexane, and can then be fed in the gas phase to the catalyst to be employed according to the invention. In many cases, it has proved appropriate if the molar ratio of the carboxylic component to hydrogen is 1:1 to 1:500, and the process is preferably carried out with a ratio of 1:5 to 1:50. The feed rate for the carboxylic acids and their derivatives is expediently 0.01 to 2 $mg/ml_{cat}$*h (LHSV: liquid hourly space velocity), and that of the hydrogen is 100 to 10,000 $h^{-1}$ (GHSV: gas hourly space velocity).

According to the present invention, aliphatic and aromatic carboxylic acids and derivatives thereof can be hydrogenated to the corresponding aldehydes. Particularly suitable derivatives are, for example, esters and anhydrides.

The process is of great interest for carboxylic compounds of the formulae (I) and (II)

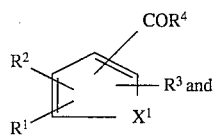  (I)

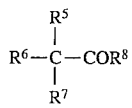  (II)

in which $R^1$ is hydrogen, straight-chain or branched $C_1$–$C_8$-alkyl, straight-chain or branched $C_1$–$C_8$-alkoxy, $R^3$-substituted phenyl, naphthyl, $R^3$- substituted phenoxy, $R^3$-substituted benzyl, $R^3$-substituted benzyloxy, hydroxyl, amino, NH-($C_1$–$C_8$-alkyl) , N-($C_1$–$C_8$-alkyl)$_2$, halogen or $COR^4$, $R^2$ is hydrogen, straight-chain or branched $C_1$–$C_8$-alkyl, straight-chain or branched $C_1$–$C_8$-alkoxy or $R^3$-substituted phenyl, or in which $R^1$ and $R^2$ together can form a fused benzene ring, which can be substituted by hydroxyl, amino, methyl, ethyl, methoxy or ethoxy, $R^3$ can be hydrogen, straight-chain or branched $C_1$–$C_8$-alkyl, straight-chain or branched $C_1$–$C_8$-alkoxy, hydroxyl, amino or halogen, $R^4$ is hydroxyl, $C_1$–$C_4$-alkoxy, chlorine, bromine or the group

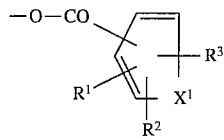

in which, in the latter case of anhydride formation, $R^1$ does not assume the meaning $COR^4$, $X^1$ is —O—, —N—, —S—, N=CH— or —CH=CH— or, $R^5$ is hydrogen or straight-chain or branched $C_1$–$C_8$-alkyl, $R^6$ is hydrogen, straight-chain or branched $C_1$–$C_8$-alkyl, $R^3$-substituted phenyl or halogen, $R^7$ is hydrogen, straight-chain or branched $C_1$–$C_8$-alkyl or $R^3$-substituted phenyl, in which the $C_1$–$C_8$-alkyl can be substituted by halogen, methoxy or ethoxy and in which $R^6$ and $R^7$ furthermore together can be dimethylene, tetramethylene or pentamethylene, and $R^8$ is hydroxyl, $C_1$–$C_4$-alkoxy, chlorine, bromine or the group —O—CO—C($R^5$, $R^6$, $R^7$).

The process is important, for example, for compounds of the formula (III)

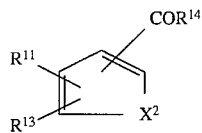  (III)

in which $R^{11}$ is hydrogen, straight-chain or branched $C_1$–$C_8$-alkyl, straight-chain or branched $C_1$–$C_8$-alkoxy, $R^{13}$-substituted phenyl, $R^{13}$-substituted phenoxy, hydroxyl, amino, NH-($C_1$–$C_8$-alkyl), N-($C_1$–$C_8$-alkyl)$_2$ or halogen, $R^{13}$ is hydrogen, straight-chain or branched $C_1$–$C_8$-alkyl, straight-chain or branched $C_1$–$C_8$-alkoxy, hydroxyl or halogen, $R^{14}$ is hydroxyl, methoxy, ethoxy or chlorine and $X^2$ is —CH=CH— or —N=CH—, preferably —CH=CH—, so that aromatic carboxylic acids or derivatives thereof which are preferably employed are those of the formula (IV)

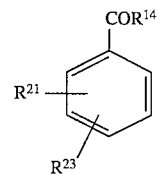  (IV)

in which $R^{21}$ is hydrogen, straight-chain or branched $C_1$–$C_4$-alkyl, straight-chain or branched $C_1$–$C_4$-alkoxy, $R^{23}$-substituted phenyl, $R^{23}$-substituted phenoxy, hydroxyl, amino, methylamino, ethylamino, dimethylamino, diethylamino, fluorine or chlorine, $R^{23}$ is hydrogen, straight-chain or branched $C_1$–$C_8$-alkyl, straight-chain or branched $C_1$–$C_4$-alkoxy, hydroxyl, fluorine or chlorine and $R^{14}$ has the abovementioned scope of meaning.

The process also has particular importance for compounds of the formula (V)

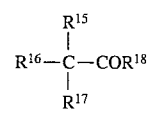  (V)

in which $R^{15}$ is hydrogen, methyl or ethyl, $R^{16}$ is hydrogen, straight-chain or branched $C_1$–$C_8$-alkyl or phenyl, $R^{17}$ is hydrogen, methyl or ethyl, or in which $R^{16}$ and $R^{17}$ furthermore together can be tetramethylene or pentamethylene, and $R^{18}$ is hydroxyl, methoxy, ethoxy or chlorine.

The process has great industrial interest if benzoic acid, chlorobenzoic acid, fluorobenzoic acid, methylbenzoic acid, methoxybenzoic acid, phenoxybenzoic acid, tert-butylbenzoic acid, p-isopropylbenzoic acid, pivalic acid, 6-methoxy-[2]-naphthoic acid or methyl or ethyl esters thereof are employed.

The aldehydes prepared according to the invention are widely used as industrial intermediates in the preparation of plant protection agents, pharmaceuticals or odiferus substances.

EXAMPLES

Catalyst A:

To prepare a coprecipitated catalyst, 361.0 g of $Al_2O_3 \cdot 9H_2O$ and 12.5 g of $SnCl_4$ are dissolved in 1.5 l of water, the solution is cooled to 5° C. and the pH of the solution is brought to pH=9 with dilute ammonia solution. The precipitate is filtered off and washed with water. Drying is carried out at 130° C. and calcining is carried out at 600° C. After comminution to particle sizes of 10 to 20 mesh, the catalyst is preformed in a stream of hydrogen at 450° C.

Catalyst B:

To prepare an impregnated catalyst, 25 g of $Al_2O_3$ is initially introduced into a flask and a solution of 200 ml of ethanol and 10 g of $Sn(O^tBu)4$ is added. After thorough mixing of the sample, the solvent is cautiously distilled off and the residue is calcined at 600° C. After shaping of the catalyst to a particle size of 10 to 20 mesh, the catalyst is preformed in a stream of hydrogen at 450° C.

Examples 1 and 2

The hydrogenations are carried out in a tubular reactor. The catalyst bed volume was 20 ml. The evaporation of the benzoic acid employed is carried out in an upstream evaporator. The GHSV, LHSV and temperature are adjusted as shown in Table 1. The reaction mixture is condensed with a condenser and analyzed by gas chromatography.

TABLE 1

| Example | Catalyst | GHSV | LHSV | Temperature | Conversion | Selectivity |
|---|---|---|---|---|---|---|
| 1 | A | 1250 | 0.13 | 380° C. | 69% | 95% |
| 2 | B | 1250 | 0.12 | 350° C. | 94% | 92% |

Examples 3 to 13

The experiments are carried out as in Examples 1 and 2. Instead of benzoic acid, other aromatic or aliphatic acids or derivatives thereof are employed. The results are shown in Table 2.

TABLE 2

| Example | Catalyst | Substrate | GHSV | LHSV | Temp. | Conversion | Selectivity |
|---|---|---|---|---|---|---|---|
| 3 | A | p-chlorobenzoic acid | 1250 | 0.12 | 380° C. | 99% | 69% |
| 4 | B | p-chlorobenzoic acid | 1250 | 0.08 | 350° C. | 97% | 66% |
| 5 | B | p-fluorobenzoic acid | 1250 | 0.10 | 380° C. | 95% | 83% |
| 6 | B | p-methoxybenzoic acid | 1250 | 0.08 | 380° C. | 96% | 58% |
| 7 | B | 6-methoxy-2-naphthoic acid | 1250 | 0.14 | 380° C. | 90% | 35% |
| 8 | B | 3-phenoxybenzoic acid | 1250 | 0.12 | 380° C. | 96% | 88% |
| 9 | B | p-isopropylbenzoic acid | 1250 | 0.06 | 350° C. | 99% | 85% |
| 10 | B | p-methylbenzoic acid | 1250 | 0.15 | 380° C. | 93% | 88% |
| 11 | B | p-tert-butylbenzoic acid | 1250 | 0.08 | 350° C. | 96% | 91% |
| 12 | B | methyl benzoate | 1250 | 0.07 | 350° C. | 91% | 87% |
| 13 | B | pivalic acid | 1250 | 0.10 | 380° C. | 93% | 82% |

We claim:

1. A process for the preparation of an aldehyde by catalytic gas phase hydrogenation of a carboxylic acid or carboxylic acid derivative, the derivative selected from the group consisting of esters, acid anhydrides, acid chlorides and acid bromides, at elevated temperature, which comprises the steps of:

applying a tin catalyst to an oxidic support material to form a catalyst, and hydrogenating the carboxylic acid or carboxylic acid derivative in the presence of the catalyst.

2. The process as claimed in claim 1, wherein the tin is employed in an atomic ratio to the oxidic support of 0.001:1 to 0.5:1.

3. The process as claimed in claim 1, wherein aluminum oxide, zirconium oxide, iron oxide, titanium oxide or yttrium oxide is used as the oxidic support.

4. The process as claimed in claim 1, wherein the hydrogenation is carried out at a temperature of 250° to 600° C.

5. The process as claimed in claim 1, wherein the hydrogenation is carried out under a pressure of 0.1 to 10 bar.

6. The process as claimed in claim 1, wherein the molar ratio of carboxylic component to hydrogen is 1:1 to 1:500.

7. The process as claimed in claim 1, wherein the feed rate for the carboxylic component is 0.01 to 2 $g/ml_{cat} \times h$ and the feed rate of the hydrogen is 100 to 10,000 $h^{-1}$.

8. Process as claimed in claim 1, wherein the carboxylic acid or carboxylic acid derivative employed is a compound of the formula (I) or (II)

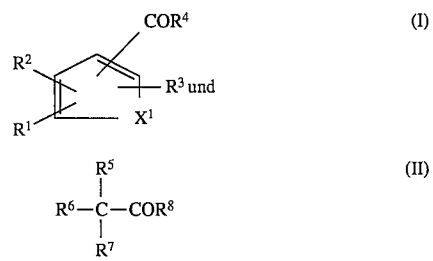

in which $R^1$ is hydrogen, straight-chain or branched $C_1$-$C_8$-alkyl, straight-chain or branched $C_1$-$C_8$-alkoxy, $R^3$-substituted phenyl, naphthyl, $R^3$-substituted phenoxy, $R^3$-substituted benzyl, $R^3$-substituted benzyloxy, hydroxyl, amino, NH-($C_1$-$C_8$-alkyl), N-($C_1$-$C_8$-alkyl)$_2$, halogen or $COR^4$, $R^2$ is hydrogen, straight-chain or branched $C_1$-$C_8$-alkyl, straight-chain or branched $C_1$-$C_8$-alkoxy or $R^3$-substituted phenyl, or in which $R^1$ and $R^2$ together can form a fused benzene ring, which can be substituted by hydroxyl, amino, methyl, ethyl, methoxy or ethoxy, $R^3$ can be hydrogen, straight-chain or branched $C_1$-$C_8$-alkyl, straight-chain or branched $C_1$-$C_8$-alkoxy, hydroxyl, amino or halogen, $R^4$ is hydroxyl, $C_1$-$C_4$-alkoxy, chlorine, bromine or the group

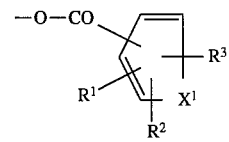

in which, in the latter case of anhydride formation, $R^1$ does not assume the meaning $COR^4$, $X^1$ is —O—, —N—, —S—, N=CH— or —CH=CH— or, $R^5$ is hydrogen or straight-chain or branched $C_1$–$C_8$-alkyl, $R^6$ is hydrogen, straight-chain or branched $C_1$–$C_8$-alkyl, $R^3$-substituted phenyl or halogen, $R^7$ is hydrogen, straight-chain or branched $C_1$—$C_8$-alkyl or $R^3$-substituted phenyl, in which the $C_1$–$C_8$-alkyl can be substituted by halogen, methoxy or ethoxy and in which $R^6$ and $R^7$ furthermore together can be dimethylene, tetramethylene or pentamethylene, and $R^8$ is hydroxyl, $C_1$–$C_4$-alkoxy, chlorine, bromine or the group —O—CO—C($R^5$, $R^6$, $R^7$).

9. The process as claimed in claim 1, wherein the aromatic carboxylic acid or derivative thereof employed is a compound of the formula (III)

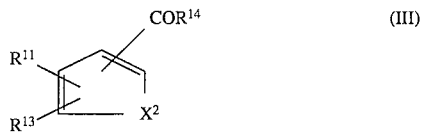
(III)

$R^{11}$ is hydrogen, straight-chain or branched $C_1$–$C_8$-alkyl, straight-chain or branched $C_1$–$C_8$-alkoxy, $R^{13}$-substituted phenyl, $R^{13}$-substituted phenoxy, hydroxyl, amino, NH-($C_1$–$C_8$-alkyl), N-($C_1$–$C_8$-alkyl)$_2$ or halogen, $R^{13}$ is hydrogen, straight-chain or branched $C_1$–$C_8$-alkyl, straight-chain or branched $C_1$–$C_8$-alkoxy, hydroxyl or halogen, $R^{14}$ is hydroxyl, methoxy, ethoxy or chlorine and $X^2$ is —CH=CH or —N=CH—, preferably —CH=CH—, so that the aromatic carboxylic acid or derivative thereof employed is preferably one of the formula (IV)

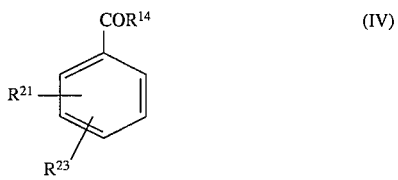
(IV)

in which $R^{21}$ is hydrogen, straight-chain or branched $C_1$–$C_4$-alkyl, straight-chain or branched $C_1$–$C_4$-alkoxy, $R^{23}$-substituted phenyl, $R^{23}$-substituted phenoxy, hydroxyl, amino, methylamino, ethylamino, dimethylamino, diethylamino, fluorine or chlorine, $R^{23}$ is hydrogen, straight-chain or branched $C_1$–$C_8$-alkyl, straight-chain or branched $C_1$–$C_4$-alkoxy, hydroxyl, fluorine or chlorine and $R^{14}$ is defined above.

10. The process as claimed in claim 1, wherein the aliphatic carboxylic acid or derivative thereof employed is one of the formula

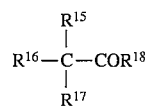
(V)

in which $R^{15}$ is hydrogen, methyl or ethyl, $R^{16}$ is hydrogen, straight-chain or branched $C_1$–$C_8$-alkyl or phenyl, $R^{17}$ is hydrogen, methyl or ethyl, or in which $R^{16}$ and $R^{17}$ furthermore together can be tetramethylene or pentamethylene, and $R^{18}$ is hydroxyl, methoxy, ethoxy or chlorine.

11. The process as claimed in claim 1, wherein benzoic acid, chlorobenzoic acid, fluorobenzoic acid, methylbenzoic acid, methoxybenzoic acid, phenoxybenzoic acid, tert-butylbenzoic acid, p-isopropylbenzoic acid, pivalic acid, 6-methoxy-[2]-naphthoic acid or the methyl or ethyl ester thereof is employed.

12. The process as claimed in claim 1, wherein the tin is employed in an atomic ratio to the oxidic support of 0.005:1 to 0.2:1.

13. The process as claimed in claim 1, wherein the hydrogenation is carried out at a temperature of from 300° to 400° C.

14. The process as claimed in claim 1, wherein the hydrogenation is carried out under a pressure of 1 bar.

15. The process as claimed in claim 1, wherein the molar ratio of carboxylic component to hydrogen is 1:5 to 1:50.

16. The process as claimed in claim 1, wherein the oxidic support material is aluminum oxide.

17. The process as claimed in claim 1, wherein the tin catalyst is applied to the oxidic support material by impregnation of the support material with a solution of a tin compound and then drying, or by coprecipitation of a solution of a tin compound and a metal salt of the support material at pH values of 6 to 10 and then filtering and drying.

18. The process as claimed in claim 17, wherein the tin compound is selected from the group consisting of tin halides, tin sulphates, tin oxalates, tin carboxylates, tin alkoxides and tin hydroxides.

19. The process as claimed in claim 17, wherein the tin compound is a di-tin or organotin compound.

20. The process as claimed in claim 17, wherein the metal salt of the support material is aluminum nitrate, zirconium oxynitrate, or zirconium oxydichloride.

21. The process as claimed in claim 17, wherein the hydrogenation is carried out at a temperature of 250° to 600° C. and under a pressure of 0.1 to 10 bar, and wherein the tin catalyst is employed in an atomic ratio to the oxidic support of 0.001:1 to 0.5:1.

22. The process as claimed in claim 1, wherein tin is the only metal catalyst used in the hydrogenation.

\* \* \* \* \*